(12) United States Patent
Lee et al.

(10) Patent No.: US 6,491,904 B1
(45) Date of Patent: Dec. 10, 2002

(54) TOPICAL COMPOSITION CONTAINING HUMAN EPIDERMAL GROWTH FACTOR

(75) Inventors: Seung Yeob Lee, Kyungsangbuk-do (KR); Jin Seok Kang, Seoul (KR); Jeom Soon Shim, Kyunggi-do (KR); Seung Wook Lim, Kyunggi-do (KR); Seung Hee Han, Kyunggi-do (KR); Byoung Kwang Lee, Kyunggi-do (KR); Young Hyo Yu, Kyunggi-do (KR); Jong Keun Chung, Kyunggi-do (KR)

(73) Assignee: Daewoong Pharmaceutical Co., Ltd., Kyunggi-do (KR)

( * ) Notice: Subject to any disclaimer, the term of this patent is extended or adjusted under 35 U.S.C. 154(b) by 0 days.

(21) Appl. No.: 09/623,559

(22) PCT Filed: Mar. 7, 1998

(86) PCT No.: PCT/KR98/00043

§ 371 (c)(1),
(2), (4) Date: Sep. 6, 2000

(87) PCT Pub. No.: WO99/44631

PCT Pub. Date: Sep. 10, 1999

(51) Int. Cl.[7] .............................................. A61K 31/74
(52) U.S. Cl. ................................ 424/78.06; 424/78.02; 424/78.03; 424/484; 424/486; 424/400; 514/772; 514/772.1; 514/772.3
(58) Field of Search .................................. 424/400, 484, 424/486, 78.02, 78.06, 78.03; 514/772, 772.1, 772.3

(56) References Cited

U.S. PATENT DOCUMENTS

| 5,427,778 A | | 6/1995 | Finkenaur et al. | |
| 5,705,485 A | * | 1/1998 | Cini et al. | ..................... 514/12 |

FOREIGN PATENT DOCUMENTS

| EP | A1312208 | 4/1989 |
| JP | A57108197 | 7/1982 |
| WO | A1-9403157 | 2/1994 |

* cited by examiner

*Primary Examiner*—Thurman K. Page
*Assistant Examiner*—Liliana Di Nola-Baron
(74) *Attorney, Agent, or Firm*—Birch, Stewart, Kolasch & Birch, LLP

(57) ABSTRACT

The present invention relates to a topical composition containing human epidermal growth factor (hEGF) and polyoxyethylene-polyoxypropylene copolymer having a viscosity of 4–10 cps at 37° C, 60 rpm as the base for topical formulation to improve the wound healing ability of hEGF.

4 Claims, No Drawings

TOPICAL COMPOSITION CONTAINING HUMAN EPIDERMAL GROWTH FACTOR

This application is the national phase under 35 U.S.C. §371 of PCT International Application No. PCT/KR98/00043 which has an International filing date of Mar. 7, 1998, which designated the United States of America.

TECHNICAL FIELD

The present invention relates to a topical composition containing human epidermal growth factor (hereinafter referred to as "hEGF"). More specifically, the present invention relates to a topical composition which comprises a polyoxyethylene-polyoxypropylene copolymer (Generic name: Poloxamer) having a viscosity of 4–10 cps at 37° C., 60 rpm as the base for topical formulation of naturally occurring HEGF or recombinant human epidermal growth factor (rhEGF). The topical composition of the present invention is useful for the treatment of cutaneous injuries including wounds, incisions, burns, etc.

BACKGROUND ART hEGF is a polypeptide which consists of 53 amino acid residues with three disulfide bonds [see, Cohen, S. J. Biol. Chem., 237, 1555–1562, 1962; Savage, C. R., J. Biol. Chem. 248, 7669–7672, 1973]. It has been reported that HEGF plays a very important role in controlling the growth of epidermal and cutaneous cells in mammal [see, Sporn, M. B. et al., Nature (London) 313, 745–747, 1985; Sporn M. B. et al., N. Engl. J. Med. 303, 878–880, 1980]. It is also invloved in the process of wound healing [see, Buckley, A. et al., Proc. Natl. Acad. Sci. USA., 82, 7340–7344, 1985] at a molecular level. Since then numerous studies related to the recovery of cutaneous wounds with HEGF have been conducted.

Although HEGF shows a good activity for stimulating the differentiation of epidermal cells in vitro, the development of formulations containing HEGF for the treatment of topical wound is very difficult due to disadvantage in that hEGF exhibits only a little effect in treating wounds when it is clinically applied to wounds. The reasons why hEGF does not show the desired sufficient effect in treating wounds in the living body are that HEGF as the protein is very unstable, particularly in the presence of water, at room temperature, and has less than one hour in half-life which is far shorter than the lag time required for the induction of DNA synthesis of cells in wound site, which is about 8–12 hour [see, J. Surg. Res., 43, 333, 1987]. Furthermore, when HEGF is applied to the skin, HEGF loses its biological activity due to the denaturation and decomposition of HEGF by proteolytic enzymes present in wound site.

In order to provide the desired wound healing effect of hEGF, it is required to continuously maintain the effective level of HEGF by applying hEGF to wound site at any time during initial few days which are most important for wound healing [see, J. Surg. Res., 43, 333, 1987, J. Lab. Clin. Med., 108, 103, 1986]. In this regard, studies to develop the sustained releasing formulation which can continuously deliver HEGF to wound site have been conducted.

As one of the results of such studies, US Patent Specification No. 4,944,948 discloses the hEGF/liposome gel formulation using neutral phospho- lipids, negative-charged phospholipids and cholesterol, which can continuously deliver HEGF to wound site; and EP Publication No. EP 0312208 discloses the aqueous formulation which comprises pharmaceutically acceptable various water- soluble or water-swellable polymers as the base to consistently release hEGF.

However, although the above-mentioned prior art publications disclose the formulations which can continuously release HEGF for 12 hours or more, they are unsuitable for utilizing in industry since they have disadvantage of a little wound healing effect in wound site.

Particularly, in EP Publication No. 0312208, by preparing the gel formulation using polymers, as the base for continuously releasing hEGF for 12 hours or more, at a high concentration, hEGF is slowly released from the gel and continuously delivered to the wound site, and further the gel formulation itself can provide the wound healing effect by forming the coat at the wound site to create the suitable moisture condition at wound site and to prevent the invasion of pathogenic organisms into wound site. However, since this gel formulation has a very high viscosity of 1,000–12,000,000 cps at room temperature, when it is applied to the wound site with rubbing, such rubbing may cause irritation at the wound site. It is very difficult to apply the formulation to the wound having large lesional area and suffering from severe pain, such as bum. Further, the gel formulation forms an excessive coat at wound site to physically inhibit the migration of epidermal cells by mitogenic activity of hEGF thereby retarding effect of hEGF on the wound healing. Therefore, the gel formulation of said prior art publication suffers from serious disadvantage that when it is clinically applied to the wound site, the wound healing effect of hEGF cannot be sufficiently provided.

As mentioned above, since the prior art topical formulations of hEGF do not exhibit the desired sufficient wound healing effect at the wound site, it is very desirable to develop the topical preparation which can sufficiently exhibit the wound healing effect of hEGF in the living body.

Thus, the present inventors have conducted numerous studies to develop the topical preparation which can exhibit a sufficient wound healing effect in the living body. As a result, we have identified that the topical preparation of hEGF using a polyoxyethylene-polyoxy-propylene copolymer having viscosity of 4–10 cps at 37° C., 60 rpm can exhibit the desired good wound healing effect of hEGF, and thus completed the present invention.

DISCLOSURE OF THE INVENTION

Thus, the present invention relates to a composition containing hEGF for topical use.

More specifically, the present invention relates to a topical composition which comprises hEGF as the active ingredient and a polyoxyethylene-polyoxypropylene copolymer having viscosity of 4–10 cps at 37° C., 60 rpm as the base for topical preparation.

In the present specification, the degree of viscosity was indicated by the dimensions of dynes/sec per $cm^2$. This dimension referred to herein, unless otherwise indicated, is in centipose (cps) as measured using a Brookfield viscometer. All viscosity values are measured at 37° C., 60 rpm unless otherwise indicated.

BEST MODE FOR CARRYING OUT THE INVENTION

The polyoxyethylene-polyoxypropylene copolymer which is used as the base in the present invention has a viscosity of 4–10 cps, preferably 4–6 cps, at 37° C., 60 rpm. When the viscosity of polyoxyethylene-polyoxypropylene copolymer is less than 4 cps, the physical healing effect which is inherent in polyoxyethylene-polyoxypropylene copolymer is lowered and the releasing rate of hEGF is excessive fast to reduce its wound healing effect. On the other hand, the viscosity of polyoxyethylene-polyoxypropylene copolymer greater than 10 cps is also undesirable since polyoxyethylene-polyoxypropylene copolymer forms an excessive coat on the wound site inhibiting the migration of epithelial cells stimulated by hEGF, thereby lowering the wound healing effect.

In the present invention, by formulating hEGF into a topical preparation for the treatment of wound using polyoxyethylene-polyoxypropylene copolymer having viscosity of 4–10 cps the coat formed from the polymer does not serve as the physical barrier during the wound healing process and exhibits the inherent physical healing effect and further induces a sufficient wound healing effect by hEGF. Therefore, the present topical formulation can exhibit a good wound healing effect when it is applied to the wound site.

The viscosity of polyoxyethylene-polyoxypropylene copolymer is determined depending on temperature and molecular weight and content of polymer. Thus, to obtain the viscosity of polyoxyethylene-polyoxypropylene copolymer of 4–10 cps at 37° C., 60 rpm, it is preferable to use polyoxyethylene-polyoxypropylene copolymer having molecular weight of about 10,000 to 15,000 in the ratio of 5–10 wt % on the basis of a total weight of the composition or to use polyoxyethylene-polyoxypropylene copolymer having molecular weight of about 7,000 to 10,000 in the ratio of 7.5–15 wt % on the basis of a total weight of the composition.

More preferably, it is suitable to adjust the viscosity within the range of 4–6 cps by using polyoxyethylene-polyoxypropylene copolymer having molecular weight of about 10,000 to 15,000 in the ratio of 5–7.5 wt % on the basis of a total weight of the composition or by using polyoxyethylene-polyoxypropylene copolymer having molecular weight of about 7,000 to 10,000 in the ratio of 7.5–12.5 wt % on the basis of a total weight of the composition.

In the topical composition according to the present invention, either of naturally occurring hEGF or recombinant hEGF can be used as the active ingredient hEGF. The content of hEGF in the composition is preferably 0.01–1,000 μg/ml, particularly 1–100 μg/ml.

Since the topical composition of the present invention composed as mentioned above is present in a liquid state at room temperature, hEGF as the pharmacologically active ingredient can be uniformly dispersed in polyoxyethylene-polyoxypropylene copolymer base. Therefore, contrary to the prior art gel formulations, when the composition of the present invention is applied to the wound site, it exhibits a good permeation of active ingredient into the wound site, and can be uniformly spread on the wound site to increase the skin area contacting with HEGF, thereby providing an excellent wound healing effect. In addition, the composition of the present invention also has advantage that since it is in a liquid state having low viscosity, it can be formulated into spray preparation, which can be applied to the wound site by simply spraying, not rubbing, and therefore, does not cause a physical irritation to the wound.

The composition according to the present invention can further contain pharmaceutically acceptable additives which can be conventionally used in preparing the topical preparation, for example, stabilizer, excipient, etc., in addition to the active ingredient hEGF and polyoxyethylene-polyoxypropylene copolymer as the base.

If required, the composition of the present invention can be stored in a lyophilized form and then dissolved in a suitable solvent when it is used. Therefore, the composition of the present invention can be stably stored for a long period.

The present invention is more specifically explained by the following examples and experiments. However, it should be understood that the present invention is not limited to these examples in any manner.

EXAMPLE 1

| | |
|---|---|
| hEGF | 5 mg |
| Poloxamer 188 | 10 g |
| methyl paraoxybenzoate | 200 mg |
| disodium hydrogen phosphate | 340.23 mg |
| sodium chloride | 832.77 mg |
| phosphoric acid | q.s. |
| purified water | q.s. |
| Total | 100 ml |

The solution was prepared by using the above-mentioned components in the given amounts according to a conventional method. Specifically, phosphate buffer was prepared from disodium hydrogen phosphate, sodium chloride and phosphoric acid. Poloxamer 188 was added to the resulting phosphate buffer and dispersed therein with stirring. Then, methyl paraoxybenzoate as the preservative and hEGF as the active ingredient were added thereto to obtain 100 ml of the topical solution according to the present invent ion.

EXAMPLE 2

| | |
|---|---|
| hEGF | 5 mg |
| Poloxamer 407 | 7.5 g |
| methyl paraoxybenzoate | 200 mg |
| disodium hydrogen phosphate | 340.23 mg |
| sodium chloride | 832.77 mg |
| phosphoric acid | q.s. |
| purified water | q.s. |
| Total | 100 ml |

Phosphate buffer was prepared by using disodium hydrogen phosphate, sodium chloride and phosphoric acid in a given amount. Poloxamer 407 was added to the resulting phosphate buffer and dispersed therein with stirring. Then, methyl paraoxybenzoate as the preservative and hEGF as the active ingredient were added thereto to obtain 100 ml of the topical solution according to the present invention.

Experiment 1

Comparison of Wound Healing Effect of hEGF Depending on the Kind of Base in Animal Wound Model Hairs on the back of rats were shaved and the depilatory agent (Neet Cream produced by 11 Dong Pharm.) was spread thereon to remove the hair. Then, streptomycin (produced by Chong Kun Dang Corp.) was injected via intramuscular route in the dose of 0.5 g/kg to rats. Rats were anesthetized by injecting sodium pentobarbital in the dose of 40 mg/kg via intraperitoneal route. The wound was induced by removing epidermis and dermis by means of operating scissors at one area having diameter of 10 mm. Then, considering that the wound site is open, the size of wound after one day from wound induction was regarded as the initial wound area.

Depending on the kinds of the bases as used, the test animals were divided into a total of 11 groups—non-treated control group, the experimental groups (Poloxamer+hEGF group, Polyvinylpyrrolidone+hEGF group, Dextran+hEGF group, Gelatin+hEGF group and Polymethacrylamide+ hEGF group), and another control group to which only the base was applied (Poloxamer group, Polyvinylpyrrolidone group, Dextran group, Gelatin group and Polymethacrylamide group). After one day from wound induction, the wound site of each test animal was treated twice a day with the test drug in an amount of 0.5 ml for each time. In the test groups, the preparation wherein hEGF is contained in the ratio of 5 mg per 100 ml of the solution, as prepared according to the same procedure as Example 2, except that the kind and amount of the base were varied, was used as the test drug. In the base control groups, the preparation as prepared according to the same procedure as Example 2, except that hEGF is excluded was used. The wound was treated with the test drugs and the area of the cutaneous wound site was measured every day. Then, the wound remaining rate by the days of treatment was obtained by calculating the ratio of the wound area measured according to the days of treatment in comparison to the initial wound area as measured after wound induction. The wound remaining rate by the days of treatment and the days of treatment were analyzed with a linear regression to calculate the 50 % healing time ($HT_{50}$) which is the days exhibiting 50% wound remaining rate. The result as obtained is described in the following Table 1.

TABLE 1

Comparison of the treatment days of wound depending on the kinds of water-soluble polymeric bases (unit: days)

| Test groups | Content (wt %) | | | |
|---|---|---|---|---|
| | 5 | 10 | 15 | 20 |
| Poloxamer*, hEGF | 3.3 | 3.8 | 4.8 | 5.3 |
| Polyvinylpyrrolidone, hEGF | 4.9 | 5.2 | 5.1 | 5.6 |
| Dextran, hEGF | 4.8 | 5.1 | 5.5 | 5.6 |
| Gelatin, hEGF | 5.4 | 5.2 | 5.3 | 5.8 |
| Polymethacrylamide, hEGF | 5.1 | 5.1 | 5.4 | 5.7 |
| Control groups | | 7.3 | | |
| Poloxamer* | 4.8 | 5.2 | 5.8 | 6.3 |
| Polyvinylpyrrolidone | 5.5 | 5.8 | 5.8 | 6.2 |
| Dextran | 5.4 | 5.7 | 6.2 | 6.2 |
| Gelatin | 5.8 | 6.1 | 6.3 | 6.5 |
| Polymethacrylamide | 5.9 | 6.1 | 6.4 | 6.2 |

Note:
Poloxamer is the generic name of polyoxyethylene-polyoxypropylene copolymer and is Poloxamer 407 having average molecular weight of 10,000–15,000.

As can be seen from the above Table 1, when Poloxamer 407 as polyoxyethylene-polyoxypropylene copolymer was used as the base in an amount of 5–10 wt % according to the present invention, it shows a very excellent wound healing effect with wound healing days of 3.3–3.8 days. Contrary to this, the use of remaining water-soluble polymeric bases provides only a slight wound healing effect.

Experiment 2
Wound Healing Effect of hEGF Depending on the Content of Polyoxyethylene-polyoxypropylene Copolymer in Animal Wound Model To determine the wound healing effect of hEGF depending on the content of polyoxyethylene-polyoxypropylene copolymer which was identified as exhibiting the best wound healing effect in Experiment 1, the test preparation produced according to the procedure of Example 2 was used according to the same method as Experiment 1. The test animals were divided into non-treated control group, Poloxamer 2.5, 5.0, 7.5, 10.0 and 12.5 wt % containing groups, and the groups containing Poloxamer in a respective content and hEGF as active ingredient. Thus, the wound healing effect depending on the content of base was determined.

TABLE 2

Comparison of the wound healing days depending on the content of polyoxyethylene-polyoxypropylene copolymer unit: days)

| Test groups | Content (wt %) | | | | |
|---|---|---|---|---|---|
| | 2.5 | 5.0 | 7.5 | 10.0 | 12.5 |
| Poloxamer 407, hEGF | 5.8 | 3.3 | 3.1 | 3.8 | 4.8 |
| Poloxamer 407 | 6.4 | 4.7 | 4.8 | 5.3 | 5.6 |
| Control groups | | | 7.2 | | |

As can be seen from the above Table 2, when the content of polyoxyethylene-polyoxypropylene copolymer is 5–10 wt %, it exhibits a good wound healing effect with the wound healing days of 3.1–3.8 days. Particularly, when the content of polyoxyethylene-polyoxypropylene copolymer is 5–7.5 wt %, it exhibits a very excellent wound healing effect with the wound healing days of 3.1–3.3 days.

From the results obtained in the above Experiments I and 2, it can be identified that among various polymers which can be conventionally used as the base for topical preparation, only polyoxyethylene-polyoxypropylene copolymer in an amount of 5–10 wt %, particularly 5–7.5 wt % can induce an excellent wound healing effect of hEGF.

Experiment 3
Viscosity of Polyoxyethylene-polyoxypropylene Copolymer Depending on the Molecular Weight As can be seen from the above Experiments 1 and 2, the wound healing effect was greatly varied depending on the content of polyoxyethylene-polyoxypropylene copolymer. In addition, the viscosity of polyoxyethylene-polyoxypropylene copolymers can be determined depending on their molecular weight and content, and temperature.

Therefore, to identify the optimal content depending on the molecular weight of polyoxyethylene-polyoxypropylene copolymers, the viscosity of the preparation containing Poloxamer 407 (average molecular weight: about 10,000–15,000), which shows the most excellent wound healing effect, in an amount of 5–10 wt % and the content of Poloxamer 188 (average molecular weight: about 7,000–10,000) as a low molecular polyoxyethylene-polyoxypropylene copolymers, which has the same viscosity as the case of Poloxamer 407, were determined by measuring the viscosity in each case according to the following procedure.

The viscosity was measured by means of Brookfield Synchro-Lectric Viscometer (Model: RVF, U.S.A.) and the test preparations were prepared according to the following methods. Poloxamer was accurately taken depending on its content and slowly introduced into a beaker containing distilled water with stirring. Stirring was continued until Poloxamer was completely dissolved. The resulting test solution was allowed to stand for 5 hours and then about 200 ml of the solution was taken, introduced into an incubator at 25° C. to 37° C. before the experiment and then used. The viscometer was vertically equipped in the vessel containing the solution, rotated for 3 minutes at the rate of 60 rpm and then recorded the numerical value on graduation of the viscometer. The experiment was repeatedly conducted three times and the average value was obtained.

TABLE 3

Viscosity of polyoxyethylene-polyoxypropylene copolymer depending on its content (unit: cps)

| | Temp. | \multicolumn{6}{c}{Content (wt %)} | | | | | |
|---|---|---|---|---|---|---|---|
| | | 5 | 7.5 | 10 | 12.5 | 15 | 20 |
| Poloxamer 407 | 25° C. | 4.5 | 6 | 11 | | | |
| | 37° C. | 4 | 6 | 10.6 | | | |
| Poloxamer 188 | 25° C. | 4.2 | 5 | 7 | 8.6 | 10 | 16 |
| | 37° C. | 3.5 | 4.1 | 5 | 6.5 | 8 | 12.5 |

As can be seen from the above Table 3, when the content of Poloxamer 407 showing a good wound healing effect is 5–10 wt %, the viscosity was measured as 4–10 cps, and in case of the preferable content of 5–7.5 wt % the viscosity was 4–6 cps. Therefore, as the base for hEGF topical preparation to treat wound, it is preferable to use polyoxyethylene-polyoxypropylene copolymer having viscosity of 4–10 cps, more preferably 4–6 cps, at 37° C.

In addition, the content of low molecular Poloxamer 188 showing the same viscosity as in case where the content of high molecular Poloxamer 407 is 5–10 wt % at 37° C. was 7.5–15 wt %. Also the content of Poloxamer 188 showing the same viscosity as in case where the more preferable content of Poloxamer 407 is 5–7.5 wt % at 37° C. was 7.5–12.5 wt %. Therefore, it can be identified that to obtain the preferable viscosity it is better to use low molecular Poloxamer 188 in an amount of 7.5–15 wt % and more preferably 7.5–12.5 wt %.

From the results obtained in the above experiments, it can be seen that among various polymers which can be used as the base in topical preparation to control the release rate of the active ingredient and to protect the wound site physically, polyoxyethylene-polyoxypropylene copolymer having viscosity of 4–10 cps, particularly 4–6 cps, at 37° C., 60 rpm can be used according to the present invention to provide the topical preparation exhibiting a good wound healing effect.

What is claimed is:

1. A skin topical composition which comprises an effective wound healing amount of human epidermal growth factor, and 5 to 7.5 wt. % of a polyoxyethylene-polyoxypropylene copolymer having viscosity of 4–10 cps at 37° C., 60 rpm and molecular weight of 10,000 to 15,000.

2. The skin topical composition according to claim 1, wherein human epidermal growth factor is contained in an amount of 0.01 to 1,000 μg/ml.

3. The skin topical composition according to claim 1, wherein the viscosity of polyoxyethylene-polyoxypropylene copolymer at 37° C., 60 rpm is 4–6 cps.

4. A skin topical composition which comprises an effective wound healing amount of human epidermal growth factor and 5 to 7.5 wt % of a polyoxyethylene-polyoxypropylene copolymer having a molecular weight of 7,000 to 10,000 and a viscosity of 4–10 cps at 37° C., 60 rpm.

* * * * *